United States Patent [19]
LeVeen et al.

[11] Patent Number: 4,529,590
[45] Date of Patent: Jul. 16, 1985

[54] PRODUCTION OF ANGIOGENETIC FACTOR

[76] Inventors: Robert F. LeVeen, 312 Lombard St., Philadelphia, Pa. 19147; Eric G. LeVeen, 321 Confederate Cir., Charleston, S.C. 29407

[21] Appl. No.: 453,795

[22] Filed: Dec. 27, 1982

[51] Int. Cl.³ .................... A61K 35/12; A61K 39/00
[52] U.S. Cl. ........................................ 424/95; 424/85
[58] Field of Search ................................ 424/85, 95

[56] References Cited

U.S. PATENT DOCUMENTS 4,229,532 10/1980 Tolbert et al. ..................... 435/41

FOREIGN PATENT DOCUMENTS 162402 4/1955 Australia .............................. 424/95

OTHER PUBLICATIONS

Brown et al., "Angiogenic Factor from Synovial Fluid . . . ", The Lancet, Mar. 29, 1980, pp. 682–685.
Ackerman et al., "Three Day Pleural Inflammation . . . ", in Chem. Abstracts, vol. 93, 1980, 231000m.
Hartveit et al., "Serum Complement Levels . . . ", in Chem. Abstracts, vol. 79, 1973, 1045m.

Primary Examiner—Nicky Chan
Assistant Examiner—Jacqueline M. Stone
Attorney, Agent, or Firm—Gipple & Hale

[57] ABSTRACT

A process for the production of tumor angiogenetic factor and the production of antigens from a purified angiogenetic factor is shown in the present invention. The production of tumor angiogenetic factor is accomplished by injecting a material of a suitable composition to initiate production of fluid in the cavity of a living animal by inciting an inflammatory response in the cavity tissues, which response is characterized by the production of granulation tissue comprised mostly of new capillaries. After the body cavity is partly filled with the exudate, the fluid is tapped out of the cavity and purified to yield angiogenetic factor. The production of antigens is accomplished by dissolving the purified angiogenetic factor in an equal volume of distilled water, reacting the dissolved angiogenetic factor in the distilled water with a gluteraldehyde solution for at least twelve (12) hours and lyophilizing resulting mixture for storage. Animals injected with the product produce antibodies which react with the purified angiogenetic factor.

18 Claims, No Drawings

PRODUCTION OF ANGIOGENETIC FACTOR

BACKGROUND OF THE INVENTION

When cancer cells grow, a substance is produced which is called tumor angiogenetic factor. This factor induces the formation of new capillaries which vascularize the cancer allowing the tumor to grow and proliferate.

The life of solid tumors can be readily divided into two distinct stages of development: (a) an avascular stage, and (b) a vascular stage. The avascular stage of solid tumors occurs while the tumor is a microscopic aggregate in the interstitial tissue of the host.

As the solid tumor grows into a densely packed spheroidal population, its configuration begins to limit its ability to exchange nutrients and waste with the host. It is at this point that a vascular existence is required by the tumor in order to fulfill its increasing needs for proliferation. The new vascularization proceeds from preformed vessels with dormant endothelial cells entering mitosis. The new capillaries have been known to advance to the tumor and penetrate the same at rates approaching 0.3 mm/day. A comparable process has been noticed in healing wounds. During the intermediate neovascularization, blood vessels penetrate the periphery of the solid tumor, and the tumor enters the vascular stage of growth. As the vascularized tumor continues to grow, it engulfs the capillaries and induces new vascular growth at its periphery.

The capillary growth originates from the host tissue notwithstanding the fact that actual vessel growth rate is determined by the angiogenetic factor produced by the tumor cell population. Angiogenetic factor has received considerable study and has been shown to have a low molecular weight ranging between 200–300 Daltons (*British Journal of Cancer*, 40:493, 1979). In the host or patient, it attaches to a carrier protein and previous studies considered the angiogenetic factor to be a nonhistone protein produced directly by tumor cells (*Biochem.* 12:3159, 1973). Other research suggests that tumor angiogenetic factor might not be produced by the tumor itself, but by the host tissue as a reaction to the presence of a cancerous growth. One fact which strongly supports this latter thesis is the phenonmonen that tumor angiogenetic factor is not produced by animal tumor cells grown in tissue culture while copious quantities of angiogenetic factor are produced when grown, in vivo, in the animal host.

Recently, an angiogenetic factor has been isolated from the joint fluid of patients with rheumatoid arthritis. This substance, which occurs in the synovial fluid of the joint inflamed by rheumatoid arthritis, is identical to tumor angiogenetic factor isolated from animals with experimental cancers. This substance in the synovial fluid has the same molecular weight as tumor angiogenetic factor, and reacts with serological tests considered specific for the latter (*Lancet*, 1:682; Mar., 1980). This is an expected circumstance since the stimulus for endothelial proliferation which is seen in inflammation and wound healing has long been considered as humoral.

The problem which is inherent in the present art is that the small quantities of tumor angiogenetic factor available by growing tumors in experimental animals has not been productive of sufficient amounts of material for clinical use or even for laboratory analysis to determine the exact chemical structure of the angiogenetic factor.

The present process thus relates to a novel method for production of tumor angiogenetic factor, which provides numerous uses relating to its ability to promote vascularization in living tissue. A further aspect of the present invention involves using the tumor angiogenetic factor to produce antigens which present a potent type of cancer therapy.

SUMMARY OF THE INVENTION

The invention utilizes a method for the rapid mass production of tumor angiogenetic factor in a purity and quantity suitable for clinical use, and from a source acceptable as a human medicant.

The tumor angiogenetic factor is produced by injecting an irritating material into a body cavity of an animal to produce exudation of fluid and an inflammatory response characterized by the production of granulation tissue comprised mostly of new capillaries. After the tissues of the animal have yielded a supply of fluid, the body cavity is tapped to remove the fluid which is then purified for angiogenetic factor.

A second inventive aspect of the present application utilizes the previously described tumor angiogenetic factor in a method to synthesize a giant molecule of angiogenetic factor which can produce neutralizing antibodies when injected into an animal. If solid tumors can only achieve their full malignant potential by neovascularization, an ability to defeat capillary proliferation by active or passive immunization of the animal would prevent adequate vascularization of the incipient tumor, and would render the tumor growth dormant or benign in character. Such control of experimental tumors has been demonstrated by other methods employing deactivation of the angiogenetic factor (*Proc. Nat. Acad. Sci.*, 77:4331, 1980; *Nature*, 297:307, 1982). This approach is often termed antiangiogenesis. Thus, the present invention appears to present a very potent type of cancer treatment, either on its own or in conjunction with more conventional types of therapy.

DETAILED DESCRIPTION OF THE INVENTION

In the best mode and preferred embodiment of the invention, angiogenetic factor is produced by inducing a prolonged inflammatory response which is stimulated by the injection of carrageenin, turpentine, milk, bacteria or other irritants into a body cavity of cattle. Carrageenin is the common name of a galactan obtained by extractions of the Rhodophyceae (red seaweeds). The structure consists of a complex mixture of several polysaccharides, the composition of which varies with the seaweed source. The basic properties are well known and can be found in the *Merck Index* (Ninth Ed., 1976). In this regard, see Guisely in "Seaweed Colloids", Kirk-Othmer *Encyclopedia of Chemical Technology*, Vol. 17 (*Interscience*, New York, 2nd. Ed., 1968) pp. 774–781 and Towle in *Industrial Gums*, R. L. Whistler Ed. (*Academia Press*, New York, 2nd. Ed., 1973) pp. 83–114, which references are incorporated herein by reference as if set forth here in full.

Cavities that have thus far been chosen, and have shown adequate response, have been pleural, peritoneal and joint cavities. The local and immediate response to the injection of carrageenin is copious exudation of fluid and an inflammatory response which is characterized by an excessive amount of granulation tissue which is comprised mostly of new capillaries. Though rarely needed, if the dose is adequate, the injection can be repeated often as twice each week, or until the necessary response has been elicited. The fluid produced by the inflammation can be yielded at the end of approximately three (3) to ten (10) days. If two (2) injections are found to be necessary in order to initiate the desired response, the second injection should be made after seven (7) days, and the fluid should be yielded on the fourteenth (14th) day. The injection of carrageenin into body cavities causes some pain which can be readily obviated by a prior injection of pontocaine or a two percent (2%) injection of xylocaine into the cavity five (5) to ten (10) minutes prior to administration of the carrageenin.

If a joint cavity of a small cow or calf is used, the exposed portion of the body cavity to which the injection is to be made, is shaved and initially painted with suitable antiseptic. Next, the skin and soft tissues are anaesthetized by an injection of one percent (1%) xylocaine. Either five (5) milliliters of two percent (2%) xylocaine or one percent (1%) pontocaine is injected into the joint space aseptically with the needle being left in situ and the syringe detached therefrom. After approximately five (5) minutes, ten (10) milliliters of a one percent (1%) solution of carrageenin is injected through the needle left in the joint space and the needle is then removed. The joint is tapped after one (1) week to yield the joint fluid.

If the pleural cavity is used in a small cow or calf, the skin over the chest of the animal is shaved and the skin painted with an antiseptic agent. The injection is made into the pleural cavity through suitable interspace between two ribs, usually between the sixth and seventh ribs (although an interspace higher or lower can be used). At this point, 25 cc of two percent (2%) solution of xylocaine or one percent (1%) pontocaine is introduced into the pleural space. After five (5) minutes, between 100 and 200 milliliters of one and one half percent to two percent (1.5% to 2%) solution of carrageenin is injected into the pleural space. Since this solution is viscid, a large gauge needle is required.

A similar procedure to that of the pleural procedure is followed for the peritoneal cavity differing only in that the injected volume of carrageenin is increased to at least 200 milliliters. The pleural or peritoneal fluid which accumulates in the respective cavity is tapped with a suitable trochar at the end of one week and the cavity is tapped dry with approximately 1,000 milliliters being yielded from a typical animal.

The tapped yielded fluid is centrifuged to remove any cells and stored at −20° C. for further extraction and testing for the presence of angiogenetic factor. Usually, a small aliquot is taken for testing of angiogenetic factor. This sample should be immediately frozen and lyophilized to dry and concentrate it if it cannot be immediately purified. The purified material is tested upon a chick chorioallantoic membrane for activity. The testing procedure is known and set forth in a publication of *British Journal of Cancer*, 40:493, 1979.

The centrifuged frozen material is further purified by extraction with $MgCl_2.2H_2O$. Enough of the solid magnesium salts is added to the fluid to bring the final concentration to approximately two moles per liter. The resulting solution is then dialized for 60–90 minutes at room temperature against one and one half (1½) volumes of glass distilled water with constant stirring. The dialysate containing magnesium chloride is then passed through a deionization column. The effluent is finally filtered through a millipore filter to remove any bacteria and further lyophilized for purification as is well-known in the art and described in the aforementioned article. Filtration to achieve purification of the angiogenetic factor is achieved by first subjecting the exudate to gel filtration on Sephadex G100 on the treated tissue homogenate which is freeze dried and this material serves as the starting material for all subsequent purification thereof. The subsequent purification consists of the following steps:

a. the first step is separating protein components by chromatography on DEAE cellulose using a convex salt gradient between 0 and 0.3 m NaCl. The end of the gradient of the column is further washed with 0.5 m NaCl.

b. The bound material is eluted with 50 mm ammonium acetate buffer (ph 3.7) after freeze drying to remove the volatile ammonium acetate buffer.

c. Since the active component is of a low molecular weight, the bound fraction is applied from an affinity column to a Biogel $P_2$ column with 10% isopropanol in water as packing and eluting solvent.

In preparing the antigen from purified angiogenetic factor, the angiogenetic factor is reacted with two tenths percent (0.2%) gluteraldehyde solution for twelve (12) hours after dissolving five (5) milligrams of the purified angiogenetic factor in distilled water. Equal volumes of the two materials should be used. The excess gluteraldehyde can be neutralized but this has been found not to be necessary. The reaction mixture is lyophilized for storage in rubber stoppered flasks containing one (1) milligram of the dried powder. Animals injected with this product produce antibodies which react with purified angiogenetic factor as can be readily demonstrated on an Ouchterlony plate.

Variations on the procedures and results described above will be apparent to one skilled in the art. For example, the inflammatory response could be produced by injections of turpentine or dead bacteria or foreign protein. Other methods for purification and isolation of angiogenetic factor are possible. Also, the angiogenetic factor could be reacted with chemicals other than gluteraldehyde which would cause covalent bonding and yield a suitable antigen.

It should be noted that the steps of the process can be interchangeable without departing from the scope of the invention. Furthermore, these steps can be interchanged and are equivalent. In the foregoing description, the invention has been described with reference to a particular preferred embodiment, although it is to be understood that the specific details shown are merely illustrative and the invention may be carried out in other ways without departing from the true spirit and scope of the following claims.

We claim:

1. In the process for the production of tumor angiogenetic factor, comprising the steps of:
   (a) locating naturally occurring body fluid containing tumor angiogenetic factor in a human:
   (b) tapping said fluid to yield a fluid; and
   (c) purifying said tapped fluid to yield a purified tumor angiogenetic factor; the improvement wherein Step (a) comprises injecting carrageenin into the body cavity of an animal species of the genus Bos, in sufficient quantity to cause production of fluid and granulation tissue comprised of new capillaries surrounding said body cavity for at least three days thereby causing the rapid mass production of tumor angiogenetic factor.

2. In the process for the production of tumor angiogenetic factor, comprising the improvements as set forth in claim 1, wherein said body cavity is a pleural cavity.

3. In the process for the production of tumor angiogenetic factor, comprising the improvements as set forth in claim 1, wherein said body cavity is a peritoneal cavity.

4. In the process for the production of tumor angiogenetic factor, comprising the improvements as set forth in claim 1, wherein said body cavity is a joint cavity.

5. In the process for the production of tumor angiogenetic factor comprising the steps of:
   (a) locating naturally occurring body fluid containing tumor angiogenetic factor in a human:
   (b) tapping said fluid; and
   (c) purifying said fluid to yield purified angiogenetic factor; the improvements wherein step (a) comprises injecting a solution of carrageenin in a concentration ranging from 1.5-2 percent with the volume of the solution ranging from 100-200 milliliters into a pleural body cavity of an animal species of the genus Bos thereby causing the rapid mass production of tumor angiogenetic factor.

6. In the process for the production of tumor angiogenetic factor, comprising the improvements as set forth in claim 5, wherein said tapping of said body fluid occurs from the range of 3 to 10 days after said injection of carrageenin.

7. In the process for the production of tumor angiogenetic factor, comprising the improvements as set forth in claim 5, wherein after seven days following said first carrageenin injection, a second injection of carrageenin is made, and said yielded fluid is tapped on the fourteenth day following said first carrageenin injection.

8. In the process for the production of tumor angiogenetic factor, comprising the improvements as set forth in claim 5, wherein said animal species is a cow.

9. In the process for the production of tumor angiogenetic factor, comprising the improvements as set forth in claim 5, wherein said animal species is a calf.

10. In the process for the production of tumor angiogenetic factor as claimed in claim 5, the improvement comprising:
   Prior to step (a), injecting an anesthesia into a body cavity of an animal species of the genus Bos;
   In step (b), tapping said cavity via a trochar to obtain said fluid; and prior to step (c), removing the cell mass from said yielded fluid by centrifuge.

11. In the process for the production of tumor angiogenetic factor comprising the improvements as claimed in claim 10, wherein the purifying step includes the additional steps of lyophilizing, drying and freezing said centrifuged fluid.

12. In the process for the production of tumor angiogenetic factor comprising the improvements as claimed in claim 10, including the steps after step (c) of:
   (d) freezing said centrifuged fluid;
   (e) purifying said frozen material by adding $MgCl_2.2H_2O$ to produce a two mole per liter concentration of a magnesium salt containing fluid;
   (f) dialyzing said magnesium salt containing fluid against $1\frac{1}{2}$ volumes of distilled water with constant stirring, producing a dialysate;
   (g) passing said dialysate through a deionization column producing an effluent;
   (h) filtering said effluent through a millipore filter producing a filtered effluent.

13. In a process for the production of tumor angiogenetic factor comprising the improvements as claimed in claim 12, wherein said filtered effluent is further lyophilized to produce a purified tumor angiogenetic factor.

14. In a process for the production of tumor angiogenetic factor comprising the improvements as set forth in claim 10, wherein said body cavity is a pleural cavity.

15. In a process for the production of tumor angiogenetic factor comprising the improvements as set forth in claim 10, wherein said body cavity is a peritoneal cavity.

16. In a process for the production of tumor angiogenetic factor comprising the improvements as set forth in claim 10, wherein said body cavity is a joint cavity.

17. In a process for the production of tumor angiogenetic factor comprising the improvements as set forth in claim 10, wherein said animals are cattle.

18. In a process for the production of tumor angiogenetic factor comprising the improvements as set forth in claim 10, wherein a second injection of carrageenin is given after said first carrageenin injection.

* * * * *